United States Patent [19]

Yano et al.

[11] Patent Number: 5,011,632
[45] Date of Patent: Apr. 30, 1991

[54] ULTRASONIC FRAGRANCE GENERATION APPARATUS

[75] Inventors: Hisato Yano; Shusa Hashimoto; Tsuyoshi Horiyama, all of Tokyo, Japan

[73] Assignee: Shimizu Construction Co., Ltd., Tokyo, Japan

[21] Appl. No.: 476,589

[22] Filed: Feb. 7, 1990

[30] Foreign Application Priority Data

Feb. 7, 1989 [JP] Japan .................................. 1-28242

[51] Int. Cl.⁵ ............................................. B01F 3/04
[52] U.S. Cl. ............................. 261/81; 261/DIG. 48; 239/102.2; 422/124
[58] Field of Search ................ 261/DIG. 48, 81; 239/102.2; 422/124

[56] References Cited

U.S. PATENT DOCUMENTS

| | | |
|---|---|---|
| 422,202 | 2/1890 | Furney . |
| 1,508,399 | 9/1924 | Kohut . |
| 1,758,552 | 5/1930 | Allen et al. . |
| 2,555,047 | 5/1951 | Logue ................................. 299/24 |
| 2,614,820 | 10/1952 | Boydjieff ............................. 261/26 |
| 2,686,944 | 8/1954 | Gubelin ............................... 21/126 |
| 2,791,994 | 5/1957 | Grieb ........................... 261/DIG. 48 |
| 2,949,900 | 8/1960 | Bodine ......................... 261/DIG. 48 |
| 3,298,674 | 1/1967 | Gilbertson ........................... 261/30 |
| 3,392,916 | 7/1968 | Engstrom ............................ 239/102 |
| 3,490,436 | 1/1970 | Hart ................................... 126/113 |
| 3,711,023 | 1/1973 | Smith .................................. 239/54 |
| 3,744,722 | 7/1973 | Burns ................................. 239/338 |
| 3,924,810 | 12/1975 | Otterstetter ....................... 239/305 |
| 3,970,250 | 7/1976 | Drews ......................... 261/DIG. 48 |
| 4,081,139 | 3/1978 | Migliozzi ........................... 239/305 |
| 4,087,495 | 5/1978 | Umehara ............................ 261/81 |
| 4,109,863 | 8/1978 | Olson et al. ....................... 239/102 |
| 4,116,387 | 9/1978 | Kremer, Jr. et al. .............. 239/338 |
| 4,301,093 | 11/1981 | Eck .................................. 239/102.2 |
| 4,303,617 | 12/1981 | Bryson ............................... 422/123 |
| 4,474,326 | 10/1984 | Takahashi ........................ 239/102.2 |
| 4,601,886 | 7/1986 | Hudgins ............................. 422/116 |
| 4,603,030 | 7/1986 | McCarthy ............................. 422/4 |
| 4,629,604 | 12/1986 | Spector .............................. 422/124 |
| 4,695,434 | 9/1987 | Spector .............................. 422/116 |

FOREIGN PATENT DOCUMENTS

| | | |
|---|---|---|
| 535375 | 3/1984 | Australia . |
| 0004039 | 9/1979 | European Pat. Off. . |
| 0123746 | 11/1984 | European Pat. Off. . |
| 0144992 | 6/1985 | European Pat. Off. . |
| 0295129 | 12/1988 | European Pat. Off. . |
| 0345149 | 12/1989 | European Pat. Off. . |
| 2832416 | 2/1980 | Fed. Rep. of Germany . |
| 2573283 | 5/1986 | France . |
| 54-119114 | 9/1979 | Japan ......................... 261/DIG. 48 |
| 62-49138 | 3/1987 | Japan . |
| 63-160660 | 7/1988 | Japan . |
| 63-308161 | 12/1988 | Japan . |
| 1-123932 | 5/1989 | Japan . |
| 1-186423 | 7/1989 | Japan . |
| 1-302047 | 12/1989 | Japan . |
| 237992 | 8/1925 | United Kingdom . |
| 1172499 | 12/1969 | United Kingdom . |

OTHER PUBLICATIONS

The American Heritage Dictionary, Apr. 1982, p. 1266.

Primary Examiner—Tim Miles
Attorney, Agent, or Firm—Oblon, Spivak, McClelland, Maier & Neustadt

[57] ABSTRACT

The present invention pertains to an ultrasonic fragrance generation apparatus for buildings, vehicles, aircraft, and the like, as well as for open areas. In particular it pertains to an ultrasonic fragrance generation apparatus by which means a suitable fragrance may be dispersed into the ambient air at a suitable time in the optimum concentration. By employing a material having increased surface area on the ultrasonic vibrating surface, it is possible with the present invention to generate a fragrant mist at an increased rate.

3 Claims, 2 Drawing Sheets

ULTRASONIC FRAGRANCE GENERATION APPARATUS

BACKGROUND OF THE INVENTION

1. Field of the Invention

The present invention pertains to an ultrasonic fragrance generation apparatus for buildings, vehicles, aircraft, and the like, as well as for open areas. In particular it pertains to an ultrasonic fragrance generation apparatus by which means a suitable fragrance may be dispersed into the ambient air at a suitable time in the optimum concentration.

2. Prior Art

Recently, there has been an increasing interest in improving the ambience in the atmosphere of living, working, traveling areas and the like through the use of fragrances. Such applications include not only masking tobacco stench and the like, but also actually exerting a physiological and psychological effect on the individuals present in the ambience.

Previously, this concept of fragrances exerting a physiological and psychological effect on human beings was known empirically as "aroma therapy". More recently, from research in the area of concomitant negative variation (CNV) of human brain waves, it has been verified that certain aromatic substances have calming, or conversely, stimulating physiological effects. For example, it has been shown that when lemon, or similar fragrances are dispersed in the air conditioning air of conference rooms, key-punch areas, and the like, that an increase in efficiency occurs and that loss of efficiency through fatigue is diminished. Similarly, rosemary and related substances have been shown to have a calming effect.

The stimulating effects of aromas related to lemon (group A), and conversely, the calming effects of rosemary and similar aromatic substances (group B), are shown below in Table 1.

TABLE 1

| Lemon Group Fragrances (A) | Rosemary Group Fragrances (B) |
| --- | --- |
| Stimulation | Sedation |
| Increased efficiency | Relaxation |
| Increased alertness | Restful sensation |
| Less fatigue | Diminished nervous tension |
| Improved concentration | |

By using appropriate fragrances and by dispersing them according to a suitable time schedule, the desired effects may be optimized. Taking the example of an office, a group A fragrance and a group B fragrance may be dispersed according to the patterns shown in FIGS. 2 and 3 respectively, whereby a fragrance or mixture of fragrances having stimulating properties are dispersed during working hours and the sedating fragrances are dispersed during break periods. In the figures, $N_0$ indicates the lowest concentration of the fragrance detectable by the human nose (threshold value) and $N_1$ indicates the concentration at which the fragrance is present during periods when its effect is not desired. It can be seen from the figures that even when the effect of the fragrance is unwanted, it is supplied at a low level below the threshold value. During the time blocks when it is desired to disperse the respective fragrance, its concentration is raised to a point above the threshold of detection by the human olfactory apparatus. Thereby, the appropriate fragrances are cycled throughout the day, each during its scheduled time zone, thus making it possible to accentuate the various "life rhythms" and at the same time, to constantly preserve the ideal ambience for the working environment. Furthermore, the advantageous properties of the various fragrances can best be used to enhance both the physical and mental well-being of those present in the controlled atmosphere.

In this way, using lemon group fragrances with mentally invigorating, stimulating (anti-drowzyness) properties, and thereby circulating an invigorating effect, lavender group fragrances with mentally calming, anti-stress, anti-anxiety, and anti-depressant properties, rosemary group fragrances with relaxing, appetite promoting properties, phytoncides with anti-microbial effects against virus and bacteria harmful to human physical well being, thus using these various fragrances and thereby enhancing the various life cycles has been proposed.

While fragrances are generally in a liquid form, the various individual components which make up a given fragrance ordinarily number in the tens to hundreds of which the volatilization properties may all be different. Therefore, when the various components making up a fragrance are allowed to volatilize naturally, those that volatilize most easily end up entering the vapor phase first. Accordingly, over time, the composition of both the fragrance given off and that of the fragrance liquid varies, and it is thus difficult to obtain the desired effect of the fragrance.

For these reasons, when supplying a fragrance to the atmospheres of buildings, vehicles, aircraft, and the like, as well as for open areas, rather that allowing the fragrant substances to volatilize spontaneously, it has recently been considered desirable to employ an ultrasonic fragrance generation apparatus or the like by which means a suitable fragrance may be dispersed into the ambient air at a suitable time in the optimum concentration, thereby dispersing the various components of the respective fragrances uniformly over time.

However, with existing ultrasonic devices for dispersing fragrances, the fragrance solution is dropped onto a vibrating surface whereby a thin liquid membrane is formed, this membrane then absorbing energy from the ultrasonic waves and thereby promptly vaporizing. With such a device, in order to disperse the fragrance efficiently, the liquid membrane formed on the vibrating surface must be formed very thin. Therefore, to increase the output, the surface area of the vibrating surface must be increased. But as the size of the vibrating surface area is increased, so must the size of the fragrance solution vaporization vessel and that of the apparatus as a whole. There are limits to the maximum suitable size for the apparatus, and thus accordingly, limits to the fragrance output for such a device.

SUMMARY OF THE INVENTION

The intent of the present invention, in light of the above problems, is to provide a ultrasonic fragrance generation apparatus in which, even when the quantity of supplied fragrance solution is increased, the apparatus is able to efficiently aerosolize the fragrance and provide it to the ambient air.

The ultrasonic fragrance generation apparatus of the present invention includes a fragrance solution vaporization vessel, an air supply device, and a fragrance solution supply device, the air supply device and fragrance solution supply device supplying pressurized air and fragrance solution respectively to the fragrance solution vaporization vessel. With the present device, the fragrance solution vaporization vessel is equipped with an ultrasonic wave generation device by which means the fragrance solution within the fragrance solution vaporization vessel is vaporized. Furthermore, the ultrasonic wave generation device includes a vibrating surface which is formed of a porous mesh material whereby the vaporization of the fragrance solution is facilitated.

Thus, the above described apparatus is not only capable of supplying a suitable fragrance for altering and improving the ambient atmosphere, but is also able to by both physiological and psychological mechanisms to ameliorate fatigue and to instill tranquility and an invigorating effect in those in the ambiance, the various effects depending on the fragrance delivered into the atmosphere. Similar, various botanical products, such as phytoncides with anti-microbial effects against virus and bacteria harmful to human physical well being may be delivered into the atmosphere.

With the ultrasonic fragrance generation apparatus of the present invention, when the fragrance solution is being vaporized, the fragrance solution supply device and the air supply device supply fragrance solution and air, respectively, in concert to the fragrance solution vaporization vessel. Thus, at the required fragrance generation rate, a balanced amount of air and fragrance solution is supplied to the fragrance solution vaporization vessel and hence to the vibrating surface which is formed of a porous mesh material. Accordingly, a suitable amount of the fragrance solution can be efficiently vaporized. The vibrating surface of the ultrasonic wave generation device is equipped with a material that greatly promotes vaporization of the solution. As the fragrance solution is supplied to this vaporization promoting material, it forms a thin membrane which then absorbs the generated ultrasonic energy and is mixed with the supplied air in a suitable ratio and is thus efficiently and rapidly vaporized.

A BRIEF DESCRIPTION OF THE DRAWINGS

DETAILED DESCRIPTION OF THE PREFERRED EMBODIMENTS OF THE PRESENT INVENTION

In the following section, an example of one preferred embodiment of the present invention will be described in detail.

Figure 1:
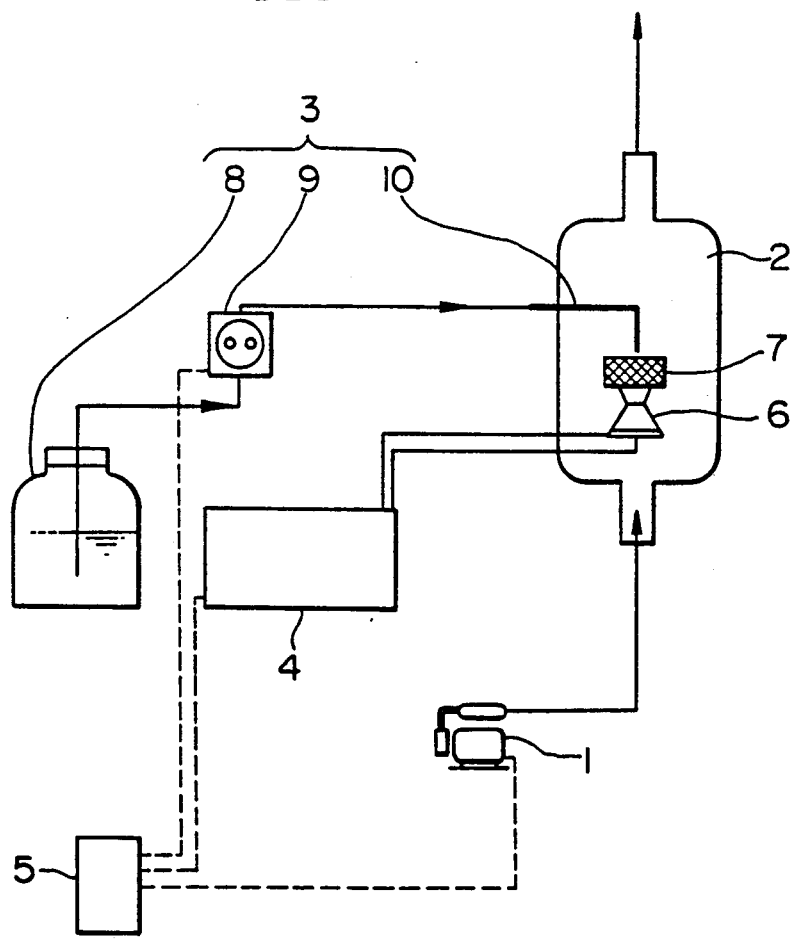
FIG. 1 is a schematic representation of the ultrasonic fragrance generation apparatus of the present invention.
Figure 2:
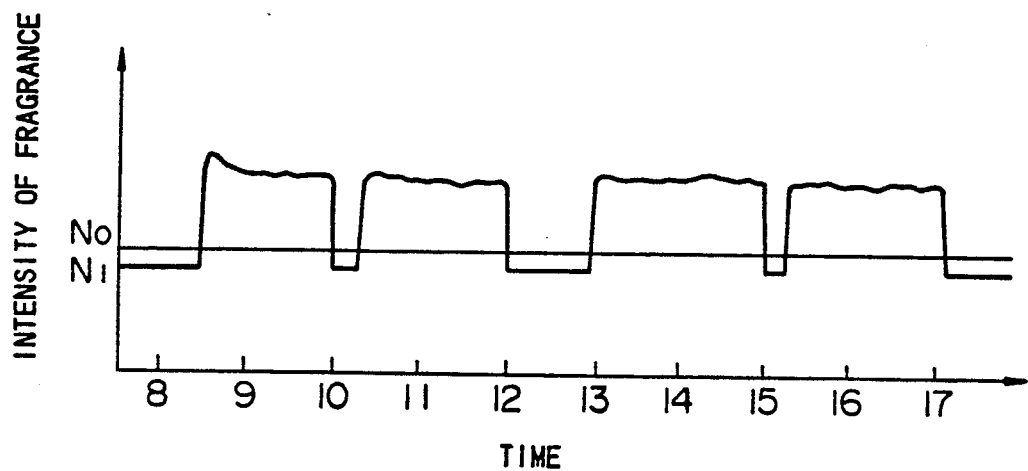
FIGS. 2 and 3 are graphs that indicate an example of a fragrance supply pattern.
Figure 3:
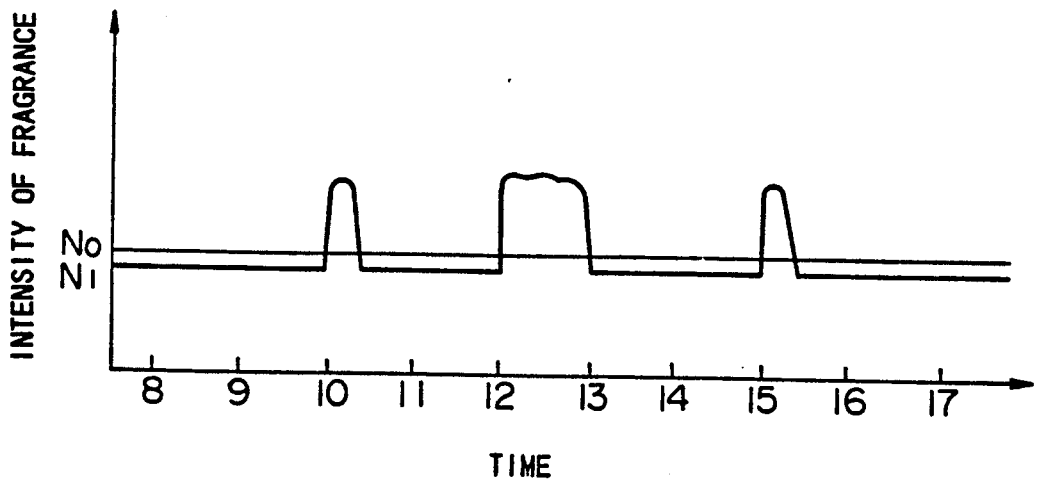

The present preferred example is schematically indicated in FIG. 1. The outflow side of air pump 1 (air supply device) is connected with an air supply pipe which is enlarged in its terminal portion to form a fragrance solution vaporization vessel 2. A fragrance solution supply device 3 supplies fragrance solution to within the fragrance solution vaporization vessel 2. An ultrasonic wave generation device 4, as well as the above mentioned air pump 1 and fragrance solution supply device 3 are controlled by a programmable controller 5.

The above mentioned ultrasonic wave generation device 4 includes a horn shaped vibrating member 6 fitted within the fragrance solution vaporization vessel 2. An oscillating circuit (indicated as part of ultrasonic wave generation device 4 in FIG. 1) is fitted to the lower part of fragrance solution vaporization vessel 2. Energy from ultrasonic waves generated from the distal most portion of the above mentioned horn shaped vibrating member 6 (ultrasonic wave generating vibrating surface) are transmitted to fragrance solution supplied by the above mentioned fragrance solution supply device 3, the fragrance solution being thereby vaporized.

On the distal most portion of the above mentioned horn shaped vibrating member 6, a vaporization promoting material 7, such as metal mesh or other net-like material is provided. This vaporization promoting material 7 is not limited to net-like material, but a porous material such as a sintered alloy, or sponge material, or other material having relatively increased surface area may be employed as well.

The above mentioned fragrance solution supply device 3 is made up of a fragrance storage tank 8 which contains the fragrance solution, a fragrance micro-delivery pump 9 which delivers fragrance solution to the fragrance solution vaporization vessel 2, and a control needle 10 which then supplies the fragrance solution to vaporization promoting material 7.

When the above described ultrasonic fragrance generation apparatus is employed to generate a fragrant atmosphere, air pump 1, fragrance micro-delivery pump 9, and ultrasonic wave generation device 4 operate in concert. Air is supplied to fragrance solution vaporization vessel 2 by means of air pump 1 while the required fragrance solution within fragrance storage tank 8 is supplied by fragrance microdelivery pump 9 in the an amount suitable for the desired delivery rate via control needle 10 to the vaporization promoting material 7 on horn shaped vibrating member 6. In this way, as fragrance solution is supplied to vaporization promoting material 7 which has an increased surface area, a solution membrane is formed over the entire surface of this vaporization promoting material 7, this solution membrane then absorbing energy from the oscillating horn shaped vibrating member 6 and thereby efficiently vaporizing. At the same time, the vapor thus formed is mixed with air thereby rapidly forming a fragrant mist. With the ultrasonic fragrance generation apparatus of the present invention, the amount of air supplied from air pump 1, the amount of fragrance solution supplied from fragrance microdelivery pump 9, as well as the energy of the generated ultrasonic waves are controlled by programmable controller 5, thereby generating the fragrant vapor at the optimum concentration. Because a porous or net-like material is used for vaporization promoting material 7, its surface area is accordingly increased and the amount of supplied fragrance solution may be increased while maintaining a thin liquid membrane and without increasing the overall size of the vibrating surface, thereby creating the fragrant mist at very high efficiency. As described above, a suitable fragrance may be supplied uniformly, at optimum concentration to the ambient air of buildings, vehicles, aircraft, the work place, and to open areas equally and uniformly dispersed through the respective atmospheres.

With the ultrasonic fragrance generation apparatus of the present invention, a plurality of fragrance solution supply devices 3 may be connected with the single fragrance solution vaporization vessel 2. By this means, a plurality of suitable fragrances may be supplied at optimum concentration during appropriate intervals as controlled by programmable controller 5.

What is claimed is:

1. An ultrasonic fragrance generation apparatus comprising:
   a fragrance solution vaporization vessel having an air inlet, a fragrant mist outlet, and a central line of air flow between said inlet and said outlet;
   an air supply device supplying pressurized air through said air inlet;
   an ultrasonic wave generation device located in said fragrance solution vaporization vessel along said central line of air flow;
   a fragrance solution supply device supplying a fragrance solution to said ultrasonic wave generation device, said ultrasonic wave generation device including a vibrating surface by which the fragrance solution is vaporized within the fragrance solution vaporization vessel; and
   a vaporization promoting material disposed above and in contact with said vibrating surface, said vaporization promoting material being of relatively increased surface area for facilitating vaporization of the fragrance solution within said fragrance solution vaporization vessel.

2. An ultrasonic fragrance generation apparatus as recited in claim 1, wherein said vaporization promoting material is formed of a porous mesh material.

3. An ultrasonic fragrance generation apparatus as recited in claim 1, said apparatus further comprising a programmable controller for generating a fragrant mist having an optimum fragrance concentration, said programmable controller including means for controlling an amount of air supplied by said air supply device, means for controlling an amount of fragrance solution supplied by said fragrance solution supply device, and means for controlling an energy level of ultrasonic waves generated by said ultrasonic wave generating device.

* * * * *